United States Patent [19]
Richmond

[11] Patent Number: 5,476,449
[45] Date of Patent: Dec. 19, 1995

[54] NEEDLELESS MULTI-LIQUID MEDICAMENT DELIVERY SYSTEM WITH MEMBRANES

[76] Inventor: Frank M. Richmond, 205 A Grant St., Harvard, Ill. 60033

[21] Appl. No.: 95,732

[22] Filed: Jul. 22, 1993

Related U.S. Application Data

[63] Continuation-in-part of Ser. No. 997,861, Dec. 28, 1992, abandoned.

[51] Int. Cl.⁶ .................................................. A61M 37/00
[52] U.S. Cl. ............................ 604/87; 604/88; 604/191
[58] Field of Search ............................ 604/82, 86–89, 604/191, 201, 203, 205, 241, 244, 416, 90–92; 128/763, 764, 770

[56] References Cited

U.S. PATENT DOCUMENTS

| | | | |
|---|---|---|---|
| 2,159,217 | 5/1939 | Lozier et al. | 604/88 |
| 2,193,322 | 3/1940 | Lozier et al. | 604/88 |
| 3,785,379 | 1/1974 | Cohen | 604/88 |
| 3,911,916 | 10/1975 | Stevens | 604/191 |
| 3,923,058 | 12/1975 | Weingarten | 604/191 |
| 4,055,177 | 10/1977 | Cohen | 604/88 |
| 4,059,109 | 11/1977 | Tischlinger | 604/88 |
| 4,361,149 | 11/1982 | Wörder | 604/202 |
| 4,392,851 | 7/1983 | Elias | 604/82 |
| 4,614,437 | 9/1986 | Buehler | 366/130 |
| 4,629,455 | 12/1986 | Kanno | 604/241 |
| 4,643,721 | 2/1987 | Brunet | 604/191 |
| 4,861,335 | 8/1989 | Reynolds | 604/88 |
| 5,102,388 | 4/1992 | Richmond | 604/88 |

OTHER PUBLICATIONS

Vaclok Medallion Syringe Brochure—Merit Medical—Salt Lake City, Utah 84107 (1992).

*Primary Examiner*—C. Fred Rosenbaum
*Assistant Examiner*—V. Alexander
*Attorney, Agent, or Firm*—John L. Rogitz

[57] ABSTRACT

A syringe for sequentially injecting a plurality of liquids into an intravenous (IV) infusion component that has a connector fitting includes a syringe vessel having a preferably needleless injection port that is engageable with the connector fitting of the IV component. A syringe plunger is slidably disposed in the syringe vessel, and at least one barrier plunger is slidably disposed in the syringe vessel between the injection port and the syringe plunger. The barrier plunger is formed with a pathway for fluid communication therethrough, and a fluid-tight membrane is positioned in the pathway of the barrier plunger to block fluid communication through the pathway. A non-sharp nipple extends inwardly from the injection port for breaking the membrane of the barrier plunge when the barrier plunger is urged against the nipple. A first liquid is disposed in the syringe vessel between the barrier plunger and the injection port and a second liquid is disposed in the syringe vessel between the two plungers. The syringe plunger can be advanced against the second liquid toward the injection port, thereby urging the barrier plunger against the first liquid to expel the first liquid through the injection port. As the syringe plunger is advanced further into the vessel, the barrier plunger is urged against the nipple of the injection port to break the membrane, thereby establishing a pathway for fluid communication through the channel of the barrier plunger for expelling the second liquid through the injection port.

16 Claims, 2 Drawing Sheets

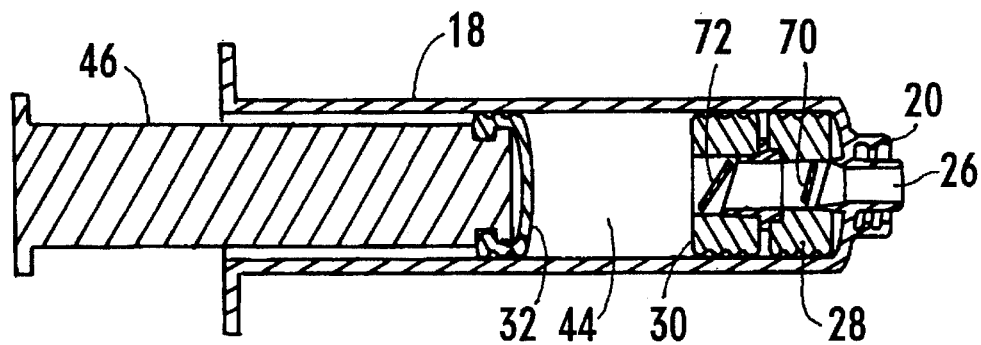
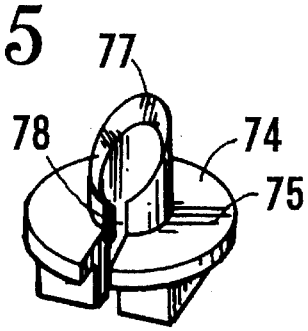
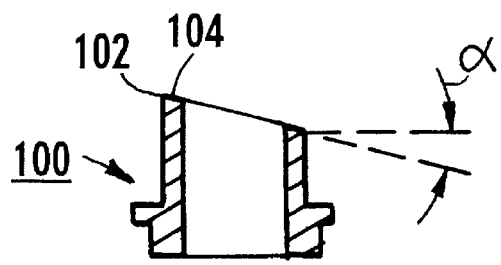
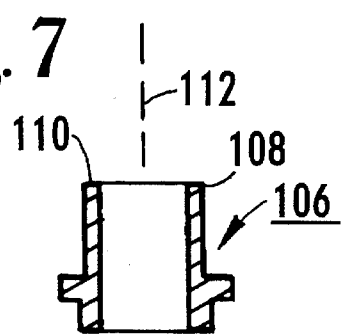
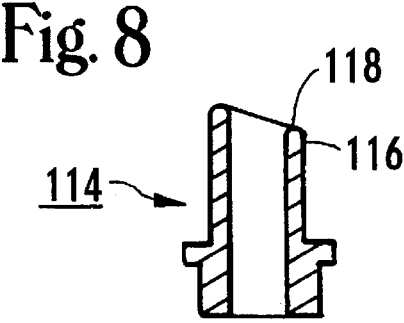

5,476,449

NEEDLELESS MULTI-LIQUID MEDICAMENT DELIVERY SYSTEM WITH MEMBRANES

RELATED APPLICATIONS

The present application is a Continuation-In-Part of and claims priority from the following U.S. patent application: Ser. No. 07/997,861 for an invention entitled "Multi-Liquid Medicament Delivery System With Membranes" filed Dec. 28, 1992, incorporated herein by reference, now abandoned.

FIELD OF THE INVENTION

The present invention relates generally to systems that deliver liquid medicaments intravenously, and more particularly to systems that deliver a plurality of liquid medicaments intravenously.

BACKGROUND

Many modern medical therapies require the intravenous (IV) infusion of liquid medicaments into the patient undergoing treatment. Typical liquid medicaments include simple saline solutions, to prevent patient dehydration, solutions containing nutrients for the patient, and solutions that contain medicinal compounds. These liquid medicaments can be infused into the patient by, e.g., gravity drain from an elevated IV bag into the patient, pumping the liquid medicament from a medicament source into the patient, or any other method which is appropriate for the particular therapy and patient.

Ordinarily, the liquid is infused into the patient by connecting the liquid source to one end of an IV line, attaching a needle to the other end of the line, and inserting the needle into the patient. Regardless of how the particular IV infusion therapy is effected, however, the need occasionally arises to infuse other medicaments, in addition to the medicament being infused, into the patient. Commonly, this means that a second needle must be inserted into the patient or injection site. It can be appreciated that this is uncomfortable for the patient and introduces addition hazard to the medical staff. Moreover, the use of needles preferably should be minimized, to minimize the chances of health care workers inadvertently puncturing themselves with needles, which can be especially nettlesome in the era of AIDS.

Accordingly, devices have been developed which permit the infusion of more than one medicament type through a single IV line. For example, connectors familiarly referred to as injection sites ("Y"-site valves or "T"-site valves because of their shape), have been introduced. A Y-site valve has a first port that can be connected to an IV line leading to the source of the liquid medicament to be infused, a second port that can be connected to an IV line leading to the patient, and a third port that can be connected to a second source of liquid medicament. Flow from the first source can be stopped, e.g., by engaging a roller clamp with the IV line leading to the source and then operating the roller clamp to collapse the line, and the infusion of liquid from the second source into the patient can be then be effected through the Y-site valve and the IV line that leads to the patient. Alternatively, a check valve can be positioned just up stream of the Y-site valve or T-site valve.

It is sometimes the case, however, that infusion of a first type of medicament through an IV line into a patient or another IV component, such as an IV bag, cannot immediately precede the infusion of a second type of medicament through the same IV line. This is because some medicaments are not compatible with certain other medicaments. Accordingly, when it is desired to infuse a second medicament into, for example, a patient, through an IV line through which a first medicament has been infused which is incompatible with the second medicament, infusion of the first medicament through the IV line must be halted. Then, a source of flushing fluid or buffer solution must be connected to the Y-site valve, and fluid infused through the Y-site valve and IV line to flush the line.

Next, the source of flushing fluid or buffer solution must be disconnected from the Y-site valve, and the source of the second medicament connected to the valve. Then, the second medicament is infused into the patient. After infusion of the second medicament, the source of the second medicament must be disconnected from the Y-site valve, the IV line flushed again, and the source of the first medicament reconnected to resume the IV therapy.

Understandably, the disconnecting and connecting of a series of IV lines to a single injection site valve can be a time-consuming, labor-intensive evolution, and can also lead to human error in connecting and disconnecting the lines in proper sequence, and potential leaking of the injection site. Such mistakes can not only result in ineffective IV infusion therapy, but can also cause grave complications in the patient.

To address these problems, several syringes have been introduced which have a plurality of chambers, with each chamber being filled with a corresponding liquid, and the syringe can then be used to inject a plurality of liquids into a receptacle. The chambers are separated by plungers which can slide within the syringe, and, as disclosed, e.g., in U.S. Pat. No. 5,102,388 to Richmond, the plungers can be punctured by needles anchored in the next successive plunger after the chamber between the plungers has been exhausted of liquid.

Unfortunately, devices such as the that disclosed in Richmond require the use of sharps in the form of puncturing needles, thus raising the possibility of puncturing personnel whose job it is to fill the chambers with liquids and then position the plungers with sharp needles within the chambers. Further, Richmond and like devices do not provide for connection to a needleless fitting, e.g., the luer fitting of an IV line.

Accordingly, it is an object of the present invention to provide a syringe for infusing a plurality of medicaments into a patient in a predetermined sequence. It is another object of the present invention to provide a syringe which reduces the need to use needles or other sharp components. A further object of the present invention is to provide a syringe for infusing a plurality of liquid medicaments into a patient in a predetermined order, without requiring repeated connections and disconnections of IV lines to an IV connector. Another object of the present invention is to provide a syringe for infusing a plurality of liquid medicaments into a patient in a predetermined order which is easy to use and cost-effective to manufacture.

SUMMARY OF THE INVENTION

A delivery system for sequentially infusing a plurality of liquid medicaments into a patient, or multiple doses of the same medicament into the patient, includes a needleless syringe vessel having a wall and an injection port formed through the wall. Preferably, the injection port is configured for engaging a needleless connector fitting of an intravenous (IV) component. The IV component can be any appropriate device, such as an IV line, an IV infusion bag, an IV infusion bottle, or an IV valved connector. Accordingly, in one preferred embodiment, the injection port includes a luer fitting for engaging a complementary connector fitting on an IV infusion component, and can thus infuse fluid into the IV infusion component without resorting to the use of needles.

As envisioned by the present invention, a syringe plunger is slidably disposed in the syringe vessel, and at least one barrier plunger is also slidably disposed in the syringe vessel between the syringe plunger and the injection port. A first liquid medicament is disposed in the syringe vessel between the barrier plunger and the injection port, and a second liquid medicament is disposed within the syringe vessel between the two plungers. Preferably, to facilitate advancing the syringe plunger into the syringe vessel, a handle is attached to the syringe plunger.

In accordance with the present invention, the barrier plunger is formed with a channel, and the channel extends through the barrier plunger. Preferably, the channel is formed coaxially with the barrier plunger. The barrier plunger also has a means for selectively blocking the channel. This blocking means is biased to a closed configuration, wherein no fluid communication is permitted to flow through the channel. Additionally, the blocking means has an open configuration, wherein a pathway for fluid communication is established through the channel, i.e., wherein a pathway is established which permits the second liquid medicament to flow through the barrier plunger to the injection port.

As intended by the present invention, the blocking means is a fluid-tight membrane that is disposed across the channel of the barrier plunger. Preferably, the membrane is formed integrally with the barrier plunger.

The injection port includes a glass, plastic, or ceramic nipple protruding inwardly toward the barrier plunger. The nipple is configured for puncturing the barrier plunger. This nipple has one or more longitudinal slots or grooves in it to eliminate trapping fluid or air between the nipple and the barrier plunger. When the syringe plunger is urged into the syringe vessel, i.e., against the second liquid medicament, fluid pressure is generated by the second liquid medicament against the barrier plunger. This in turn causes the barrier plunger to slide within the syringe vessel toward the injection port and thus to urge against the first liquid medicament, which expels the first liquid medicament through the injection port and out of the syringe vessel.

As the syringe plunger is advanced further towards the injection port, the barrier plunger eventually abuts against the nipple of the injection port, thereby breaking the membrane of the barrier plunger. In other words, when the barrier plunger is urged against the nipple of the injection port, the nipple of the injection port breaks the membrane of the barrier plunger. This establishes a hole in the membrane and thereby permits the second liquid medicament to flow through the channel of the barrier plunger and out of the injection port as the syringe plunger is advanced further toward the injection port.

In accordance with the above disclosure, the first liquid medicament can be a saline solution for flushing the residue of earlier-infused medicaments out of the IV connector fitting into which the first liquid medicament is infused. On the other hand, the second liquid medicament can be a medicament which may not be compatible with the earlier-infused medicaments but which may nevertheless be safely infused into a patient through the IV connector fitting because of the flushing effect of the first liquid medicament.

If desired, yet a third liquid medicament can be held within the syringe vessel and expelled from the vessel through the injection port after the first and then the second liquid medicaments have been expelled. When a third liquid medicament is to be used, a third plunger is slidably disposed in the syringe vessel between the second liquid medicament and the syringe plunger, and the third liquid is disposed in the syringe vessel between the syringe plunger and the third plunger.

Like the barrier plunger, the third plunger has a channel formed therethrough and a membrane disposed in the channel for selectively blocking fluid communication through the channel. A nipple is formed on the barrier plunger to break the membrane of the third plunger when the third plunger is urged against the barrier plunger. More particularly, when the second medicament has been ejected from the syringe, the barrier plunger rests against the nipple of the injection port. As the syringe plunger is advanced further into the syringe, the third plunger is forced against the nipple of the barrier plunger, and the membrane of the third plunger is thereby broken. Consequently, a path for fluid communication is established for the third fluid to be expelled from the syringe injection port through the open channels of the third plunger and the barrier plunger. Additional plungers and medicaments can be disposed in the syringe in accordance with the principles of the present invention.

The details of the construction of the present invention, as well as the operation of the present invention, can best be understood in reference to the accompanying drawings, in which like numerals refer to like parts, and in which:

BRIEF DESCRIPTION OF THE DRAWINGS

FIG. 4 is another cross-sectional view of the liquid medicament delivery system of the present invention, as would be seen along the line 2—2 in FIG. 1, with the handle advanced into the syringe further than as shown in FIG. 3;

FIG. 5 is an isometric view of a nipple of the present invention;

FIG. 6 is a cross-sectional view of an alternate embodiment of the nipple of the present invention;

FIG. 7 is a cross-sectional view of another alternate embodiment of the nipple of the present invention; and FIG. 8 is a cross-sectional view of still another alternate embodiment of the nipple of the present invention.

DESCRIPTION OF THE PREFERRED EMBODIMENT

Figure 1:
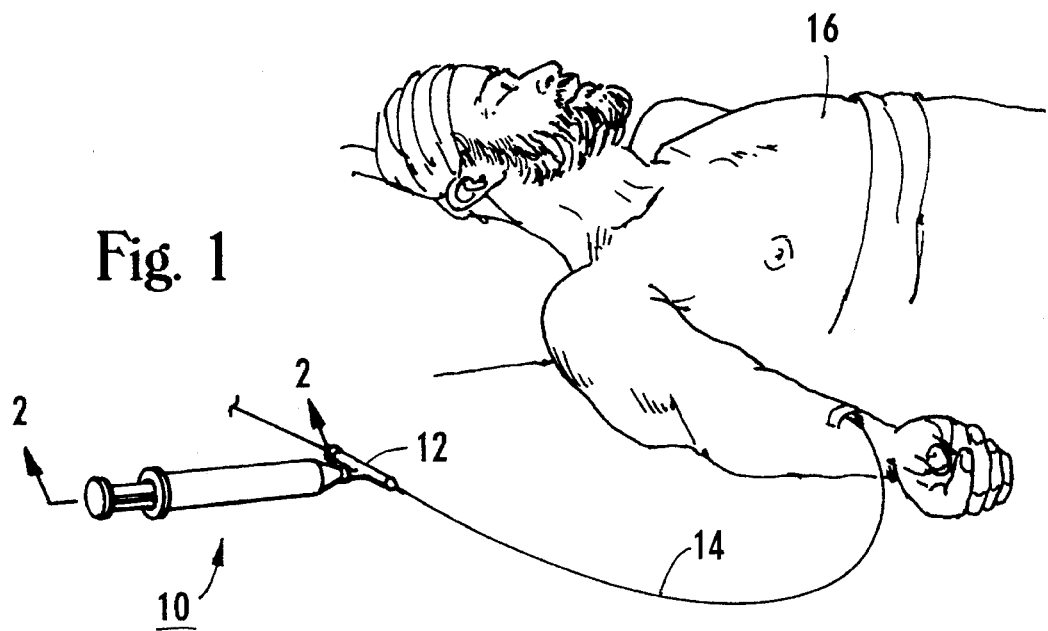
FIG. 1 is a perspective view of the liquid medicament delivery system of the present invention, shown in one intended environment.

Referring initially to FIG. 1, a liquid medicament delivery system is shown, generally designated 10. As shown, the delivery system 10 can be engaged with a suitable intravenous (IV) infusion connector, such as the Y-site valve 12, for infusing liquid from the delivery system 10 through an IV line 14 into a patient 16. Preferably, the Y-site valve is a needleless connector, i.e., the ports of the Y-site valve are configured for engaging another complementary needleless connector, such as a luer fitting.

Figure 2:
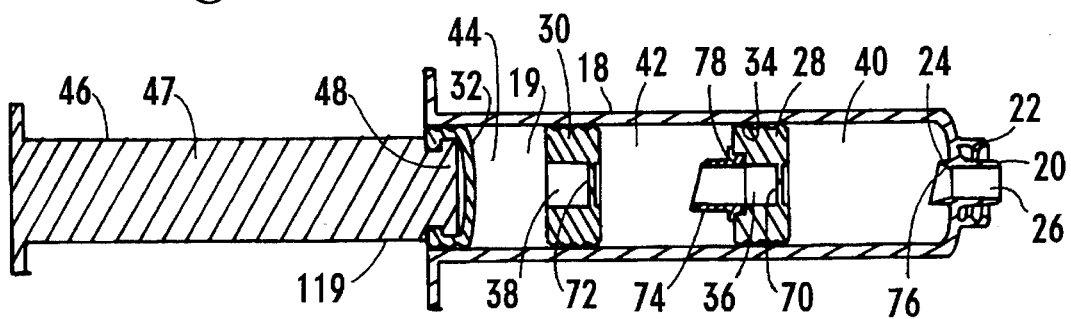
FIG. 2 is a cross-sectional view of the liquid medicament delivery system of the present invention, as seen along the line 2—2 in FIG. 1.

Referring now to FIG. 2, the details of the system 10 can be seen. As shown in FIG. 2, the system 10 is essentially a syringe having a plurality of fluid medicaments therein. More specifically, the system 10 includes an elongated, generally cylindrical syringe vessel 18 forming a chamber 19, and the vessel 18 has a port 20 formed in one end thereof. Preferably, the port 20 includes a luer fitting 22 for engaging a complementary luer fitting (e.g., one of the luer fitting on the Y-site valve 12). The luer fitting 22 can be a male luer fitting, as shown, or a female luer fitting, as appropriate for the particular application of the system 10.

Additionally, FIG. 2 shows that the port 20 has an inwardly-protruding nipple 24. A passageway 26 is established by the port 20 for permitting fluid communication out of the chamber 19 through the passageway 26. The syringe vessel 18 and associated port 20 are made of a biocompatible material, such as transparent glass or plastic, that is suitable for use as a syringe.

FIG. 2 shows that the system 10 has a plurality of plungers for sequentially urging a plurality of fluids out of the chamber 19. In the embodiment shown, three plungers are serially disposed in the chamber 19. More particularly, first and second barrier plungers 28, 30 are slidably disposed in the chamber 19, and a syringe plunger 32 is slidably disposed in the chamber 19. Each plunger 28, 30, 32 is made of a biocompatible resilient material, such as rubber, silicone, or urethane.

As can be appreciated in reference to FIG. 2, each plunger 28, 30, 32 is generally formed as a disc. Each plunger 28, 30, 32 has a plurality of ring-like lands that engage the inside wall of the syringe vessel 18 in an interference fit to form a fluid-tight seal between the particular plunger 28, 30, 32 and the syringe vessel 18. For example, the first barrier plunger 28 has lands 34 that engage the inside wall of the syringe vessel 18 in an interference fit to form a fluid-tight seal between the first barrier plunger 28 and the syringe vessel 18.

FIG. 2 further shows that each of the barrier plungers 28, 30 has a respective channel 36, 38 formed therethrough that establishes a pathway for fluid communication therethrough. Each channel 36, 38 is preferably coaxial with its respective plunger 28, 30. Moreover, means are provided in each plunger 28, 30 for blocking the associated channel 36, 38, as described more fully below.

In accordance with the disclosure above, it can be appreciated that a plurality of fluid medicaments can be held in the chamber 19 of the syringe vessel 18 separate from each other. Specifically, a first fluid 40 is held in the chamber 19 between the first barrier plunger 28 and the port 20. Also, a second fluid 42 is held in the chamber 19 between the first barrier plunger 28 and the second barrier plunger 30. Further, a third fluid 44 is held between the second barrier plunger 30 and the syringe plunger 32. These fluids 40, 42, 44 cannot mix with each other because of the fluid-tight seals between the fluids 40, 42, 44 which are established by the plungers 28, 30, 32. Consequently, the fluids 40, 42, 44 do not have to be compatible with each other. It is to be understood that each of the fluids 40, 42, 44 can be any appropriate fluid, e.g., saline solution, heparin, medicinal compound, etc., for IV infusion to the patient 16.

Still referring to FIG. 2, a handle 46 is connected to the syringe plunger 32 for providing a means for advancing the syringe plunger 32 into the chamber 19 of the syringe vessel 18. Preferably, the handle 46 has an elongated shank 47 that is made of rigid plastic. To connect the handle 46 to the syringe plunger 32, the distal end 49 of the handle 46 is formed with a head 48, and the head 48 is embedded in the syringe. If desired, the head 48 of the handle 46 can be bonded or screwed to the syringe plunger 32. While FIG. 2 indicates that the head 48 is formed separately from the handle 46, it is to be understood that for ease of manufacture, the head 48 can be formed integrally with the handle 46.

As mentioned above and shown in FIG. 2, the first and second barrier plungers 28, 30 include means for selectively blocking their respective channels 36, 38. Specifically, as shown in FIG. 2, each channel 36, 38 has a respective fluid-tight membrane 70, 72 positioned therein for selectively blocking the channel 36, 38. The membranes 70, 72 are substantially identical in construction and operation. Preferably, each membrane 36, 38 is formed integrally with its respective plunger 28, 30.

A nipple 74 is attached to the first barrier plunger 28 and extends toward the-channel 38 of the second barrier plunger 30. The nipple 74 can slide within the channel 38 of the second barrier plunger 30 and is configured for breaking the membrane 72 of the second barrier plunger 30 when the second barrier plunger 30 is urged against the nipple 74.

As shown best in FIG. 5, the nipple 74 has a disc-shaped base 75 and a generally frusto-conical shaped protrusion 77, although other suitable configurations that are appropriate for breaking, e.g., puncturing, the membrane 72 can be used. The nipple 74 is hollow, so that fluid can flow through the nipple 74 to the channel 36 of the first barrier plunger 28. As shown in FIG. 5, at least one groove 78 is formed longitudinally in the protrusion 77, to prevent trapping fluid between the nipple 74 and the plunger 30. If desired, the groove 78 can extend radially into the base 75. Likewise, at least one groove 76 (FIG. 2) may be formed in the nipple 24.

In the operation of the system 10, reference is made to FIGS. 1 and 2. The luer fitting 22 of the system 10 is engaged with a component, e.g., the Y-site valve 12, through which it is desired to infuse fluid from the system 10.

Next, an operator (not shown) advances the syringe plunger 32 into the syringe vessel 18 by appropriately manipulating the handle 46. As the syringe plunger 32 is advanced into the syringe vessel 18 the third fluid 44 is pressurized, causing the third fluid 44 to in turn urge against the second barrier plunger 30. The second barrier plunger 30 is thereby caused to urge against the second fluid 42, which causes the second fluid 42 to urge against the first barrier plunger 28. The first barrier plunger 28 in turn is caused to advance into the first fluid 40, causing the first fluid 40 to be expelled through the fluid passageway 26.

Stated differently; when the system 10 is configured as shown in FIG. 2, a hydraulic lock exists within the syringe vessel 18. When the operator urges against the handle 46 to advance the syringe plunger 34 into the syringe vessel 18, the hydraulic lock transfers this force through the second and third fluids 42, 44 and the barrier plungers 28, 30 to cause the first fluid 40 to be expelled from the system 10 through the passageway 26.

Figure 3:
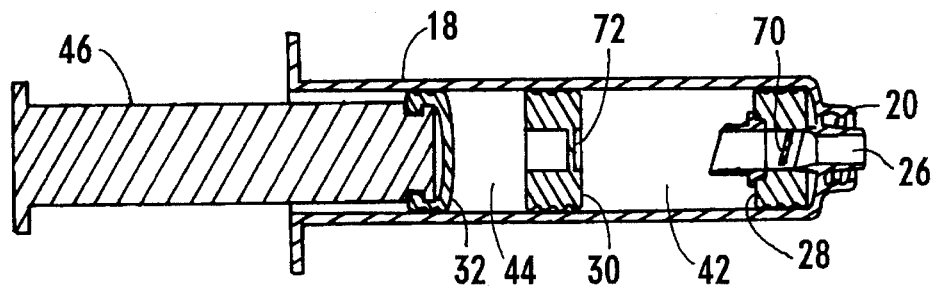
FIG. 3 is a cross-sectional view of the liquid medicament delivery system of the present invention, as would be seen along the line 2—2 in FIG. 1, with the handle partially advanced into the syringe further than as shown in FIG. 2.

As shown in FIG. 3, when the first barrier plunger 28 has been advanced sufficiently toward the port 20, the nipple 24 engages the channel 36 of the first barrier plunger 28 and breaks the membrane 70 of the first barrier plunger 28. Any residual first fluid 40 is not trapped between the first barrier plunger 28 and the syringe vessel 18, but instead flows proximally through the groove 76 of the nipple 24 of the port 20 and out of the port 20.

It will be appreciated that once the nipple 24 has broken the membrane 70 of the first barrier plunger 28, a passageway is established for the second fluid 42 to flow through the channel 36 of the first barrier plunger and out of the port 20.

Accordingly, to expel the second fluid 42 from the syringe vessel 18, the operator advances the syringe plunger 32 further into the syringe vessel 18. In other words, the operator urges against the handle 46 to advance the syringe plunger 32 into the syringe vessel 18, to expel the second fluid 42 through the channel 36 of the first barrier plunger 28 and port 20.

As shown in FIG. 4, when the syringe plunger 32 is advanced sufficiently into the syringe vessel 18, the channel 38 of the second barrier plunger 30 engages the nipple 74 of the first barrier plunger 28, thereby breaking the membrane 72 of the second barrier plunger 30. Residual second fluid 42 is not trapped between the barrier plungers 28, 30, but flows through the grooves 78 of the nipple 74 of the first barrier plunger 28 and into and through the channel 36 of the first barrier plunger 28.

At this point, it will be appreciated that once the nipple 74 has broken the membrane 72 of the second barrier plunger 30, a passageway is established for the third fluid 44 to flow through the Channels 36, 38 of the barrier plungers 28, 30 and out of the port 20.

To expel third fluid 44 from the system 10, the operator urges against the handle 46 to advance the syringe plunger 3 into the third fluid 44. This causes the third fluid 44 to be expelled through the channels 36, 38 of the barrier plungers 28, 30 and through to port 20.

In accordance with the above disclosure, it can be appreciated that the present invention provides for the sequential infusion of two or more fluids that are held in a single syringe into an IV connector and thence into an IV line or other IV component. Thus, multiple doses of a single medicament can be held in the syringe and infused without undue danger of over-infusion of more than a single dose at one time.

Now referring to FIGS. 6, 7, and 8, alternate embodiments of nipples are shown which can be used in place of the nipple 74 shown in FIG. 2. It can be appreciated in reference to FIGS. 6, 7, and 8 that the present invention contemplates the use of non-sharp, i.e., blunt or dull nipples, to reduce the likelihood of inadvertent punctures of medical personnel. Owing to the reduced thickness of the frangible membranes of the present invention, however, the nipples disclosed below can nevertheless break the membranes to establish respective pathways for fluid communication through the membranes.

More particularly, a nipple 100 is shown in FIG. 6 which has a non-sharp distal end 102. The distal end 102 has a bevel angle α with respect to the transverse dimension of the nipple 100 of less than about twenty (20) degrees. Also, the distal end 102 has a flat and, hence, a blunt surface 104. Accordingly, with this combination of structure, it is highly unlikely that the nipple 100 could puncture human skin when handled by medical personnel during manufacture or syringe preparation.

FIG. 7 shows a nipple 106 that has a distal end 108 which has a flat and, hence, blunt or dull surface 110 which is perpendicular to the longitudinal axis 112 of the nipple 106. Accordingly, with this combination of structure, it is highly unlikely that the nipple 106 could puncture human skin when handled by medical personnel during manufacture or syringe preparation.

FIG. 8 shows that a nipple 114 can have a bevelled distal end 116, and that the distal end 116 has a rounded and, hence, a blunt or dull surface 118. Consequently, it is highly unlikely that the nipple 114 could puncture human skin.

While the particular multi-liquid medicament delivery system as herein shown and described in detail is fully capable of achieving the above-stated objects, it is to be understood that it is but one embodiment of the present invention, that other embodiments are fully contemplated by the present invention, and that the scope of the present invention is accordingly to be limited by nothing other than the appended claims.

I claim:

1. A multi-liquid medicament delivery system, comprising:

a syringe vessel having a wall and an injection port formed through the wall, the injection port having a nipple formed with a non-sharp end;

a syringe plunger slidably disposed in the syringe vessel;

a barrier plunger slidably disposed in the syringe vessel between the syringe plunger and the injection port, the barrier plunger including a channel; and frangible means for blocking the channel of the barrier plunger, the frangible means being ruptured by the non-sharp end of the nipple when the frangible means is urged against the non-sharp end for establishing a pathway for fluid communication through the channel.

2. The system as recited in claim 1, further comprising a first liquid disposed in the syringe vessel between the barrier plunger and the injection port, and a second liquid disposed in the syringe vessel between the syringe plunger and the barrier plunger, for sequential expulsion of the liquids from the syringe vessel.

3. The system as recited in claim 2, wherein the nipple protrudes inwardly toward the barrier plunger.

4. The system as recited in claim 3, wherein the frangible means is a fluid-tight membrane positioned in the channel of the barrier plunger, and the membrane can be broken to establish an open configuration of the membrane when the barrier plunger is urged against the nipple of the injection port.

5. The system as recited in claim 4, further comprising a handle attached to the syringe plunger.

6. The system as recited in claim 5, wherein the handle is configured for gripping such that the handle can be manipulated to urge the syringe plunger into the second liquid toward the injection port, thereby urging the barrier plunger into the first liquid to expel the first liquid through the injection port.

7. The system as recited in claim 1, wherein the injection port includes a needleless fitting for engaging a complementary needleless fitting.

8. The system as recited in claim 7, wherein the needleless fitting is a luer fitting for engaging a complementary luer fitting.

9. A syringe for sequentially injecting a plurality of liquids into an intravenous (IV) infusion component, comprising:

a syringe vessel having an injection port;

a syringe plunger slidably disposed in the syringe vessel;

a barrier plunger slidably disposed in the syringe vessel between the injection port and the syringe plunger, the barrier plunger being formed with a pathway for fluid communication through the barrier plunger;

a fluid-tight membrane positioned in the pathway of the barrier plunger to block fluid communication therethrough; and a nipple having a blunt end extending inwardly from the injection port, the blunt end of the nipple breaking the membrane of the barrier plunger when the barrier plunger is urged against the nipple.

10. The syringe of claim 9, further comprising a first liquid disposed in the syringe vessel between the barrier plunger and the injection port and a second liquid disposed in the syringe vessel between the two plungers.

11. The syringe of claim 10, further comprising a third plunger slidably disposed in the syringe vessel between the second liquid and the syringe plunger, and a third liquid disposed in the syringe vessel between the syringe plunger and the third plunger, the third plunger having a channel formed therethrough and a membrane disposed in the channel for selectively blocking fluid communication through the channel of the third plunger.

12. The syringe of claim 11, further comprising a handle attached to the syringe plunger.

13. The syringe as recited in claim 12, wherein the injection port includes a luer fitting for engaging a complementary luer fitting.

14. A system for holding a plurality of liquids and sequentially expelling the liquids from the system into a needleless connector fitting of an IV component, comprising:

a syringe vessel having an injection port engageable with the connector fitting of the IV component, the vessel holding a first liquid and a second liquid;

a barrier plunger slidably disposed in the syringe vessel between the two liquids, the barrier plunger being formed with a pathway for fluid communication through the barrier plunger;

a fluid-tight membrane positioned in the pathway of the barrier plunger to block fluid communication therethrough; and a nipple having a non-sharp end extending inwardly from the injection port, the end of the nipple breaking the membrane of the barrier plunger when the barrier plunger is urged against the nipple.

15. The system of claim 14, further comprising a syringe plunger slidably disposed in the syringe vessel with the second liquid being disposed between the syringe plunger and the barrier plunger, the syringe plunger having a handle attached thereto for grasping the handle and urging the syringe plunger toward the injection port of the syringe vessel, thereby urging the barrier plunger toward the first liquid to expel the first liquid through the injection port.

16. The system of claim 15, further comprising a third plunger slidably disposed in the syringe vessel between the second liquid and the syringe plunger, and a third liquid disposed in the syringe vessel between the syringe plunger and the third plunger, the third plunger having a channel formed therethrough and a membrane disposed in the channel for selectively blocking fluid communication through the channel of the third plunger.

* * * * *